United States Patent [19]

Kelley

[11] Patent Number: 5,166,209
[45] Date of Patent: Nov. 24, 1992

[54] PHARMACOLOGICALLY ACTIVE COMPOUNDS

[75] Inventor: James L. Kelley, Raleigh, N.C.

[73] Assignee: Burroughs Wellcome Co., Research Triangle Park, N.C.

[21] Appl. No.: 598,494

[22] Filed: Oct. 16, 1990

Related U.S. Application Data

[63] Continuation-in-part of Ser. No. 513,311, Apr. 20, 1990, abandoned.

[30] Foreign Application Priority Data

Apr. 21, 1989 [GB] United Kingdom ................ 8909136

[51] Int. Cl.$^5$ .................. A61K 31/415; C07D 471/04
[52] U.S. Cl. ..................................... 514/300; 546/117
[58] Field of Search ......................... 546/117; 514/300

[56] References Cited

U.S. PATENT DOCUMENTS

| | | | |
|---|---|---|---|
| 3,929,812 | 12/1975 | Denzel et al. | 546/117 |
| 3,971,800 | 7/1976 | Denzel et al. | 546/117 |
| 3,971,801 | 7/1976 | Denzel et al. | 546/117 |

FOREIGN PATENT DOCUMENTS

| | | |
|---|---|---|
| 14302/88 | 10/1988 | Australia . |
| 0157637A2 | 10/1985 | European Pat. Off. . |
| 0245997A3 | 11/1987 | European Pat. Off. . |
| 0259782A1 | 3/1988 | European Pat. Off. . |
| 0281254A1 | 9/1988 | European Pat. Off. . |
| 0286278A1 | 10/1988 | European Pat. Off. . |
| 0288431A1 | 10/1988 | European Pat. Off. . |
| 2521920 | 12/1975 | Fed. Rep. of Germany . |
| 1486139 | 9/1977 | United Kingdom . |

OTHER PUBLICATIONS

Kelley, et al., Journal of Medicinal Chemistry, 1988, vol. 31, No. 5, pp. 1005-1009, 9-(2-Fluorobenzyl-)-6-(alkylamino)-9H-purines. A New Class of Anticonvulsant Agents.

Kelley, et al., Journal of Medicinal Chemistry, 1986, vol. 29, pp. 1133-1134, 9-(2-Fluorobenzyl)-6-(methylamino)-9H-purine Hydrochloride. Synthesis and Anticonvulsant Activity.

Kelley, et al., Journal of Heterocyclic Chemistry, 1988, vol. 25, pp. 1255-1258, Synthesis and Anticonvulsant Activity of 1-Benzyl-4-alkylamino-1H-imidazo[4,5-c]pyridines.

Kelley, et al., Journal of Medicinal Chemistry, 1988, vol. 31, No. 3, pp. 606-612, 6-(Alkylamino)-9-benzyl-9H-purines. A New Class of Anticonvulsant Agents.

Kelley, et al., Journal of Heterocyclic Chemistry, 1986, vol. 23, pp. 1189-1193, Synthesis of 9-(2-Fluorobenzyl)-6-(methylamino)-9H-purine.

Abstract CA52:9072D—B. W. Ashton and H. Suschitsky—carbazole synthesis of certain triazoles, none of which are encompassed by the general formula. 1960.

Woodbury, et al., Arch. int. pharmacodyn., 1952, XCII, No. 1, pp. 97-107, Design and Use of a New Electroshock Seizure Apparatus and Analysis of Factors Altering Seizure Threshold and Pattern (1).

Houston, et al., J. Med. Chem., 1985, 28, pp. 467-471, Potential Inhibitors of S-Adenosylmethionine-Dependent Methyltransferases. 8. Molecular Dissections of Carbocyclic 3-Deazaadenosine as Inhibitors of S-Adenosylhomocysteine Hydrolasse[1a].

Primary Examiner—Johann Richter
Attorney, Agent, or Firm—Donald Brown; Lawrence A. Nielsen

[57] ABSTRACT

This invention describes the preparation and use of anticonvulsant agents. In particular, triazolopyridine compounds are described which have utility in the treatment of epilepsy in mammals.

33 Claims, No Drawings

PHARMACOLOGICALLY ACTIVE COMPOUNDS

This is a continuation-in-part of application Ser. No. 07/513,311 filed on Apr. 20, 1990, now abandoned.

The present invention relates to triazolopyridines, to pharmaceutical compositions containing them, and to methods for their preparation, to their use in medicine and to methods of treating mammals.

European patent application no. 85302321.6, published under no. 157637 disclosed a class of 6-amino-9-(fluorobenzyl)-9H-purines as having anticonvulsant activity. 3-deazapurines have been reported (J. Heterocyclic Chem., 25, 1255 (1988)) to have anticonvulsant activities.

European patent application no. 88810212.6, published under no. 0288431 discloses a class of 3H-1,2,3-triazolo[4,5-d] pyrimidines as anticonvulsant agents.

Epilepsy is a collective designation for a group of chronic central nervous system disorders having in common the occurrence of sudden and transitory episodes (seizure) of abnormal phenomena of motor (convulsions), sensory, autonomic or psychic origin. The seizures are nearly always correlated with abnormal electrical activity of the brain.

The incidence of epilepsy is estimated to be approximately 1% of the total world population. A fairly large proportion (10-20%) is not adequately controlled by currently available therapies; such patients are described as refractory. Those drugs which are currently available to the medical practitioner suffer from severe limitation in use and also have a number of side effects. It is therefore clearly apparent that there is a need for new antiepileptic drugs.

The present invention is directed to a series of novel triazolopyridines which have potent anticonvulsant activity.

Accordingly, in a first aspect of the present invention there is provided compound of formula I

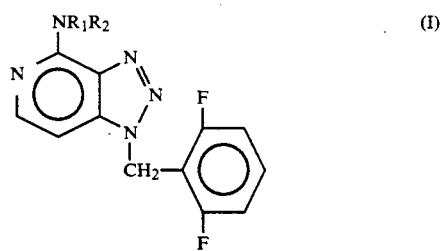

or a salt(preferably a pharmaceutically acceptable salt thereof), where $R_1$ and $R_2$ may be the same or different and are selected from hydrogen, $C_{1-4}$ straight or $C_{1-4}$ branched alkyl. Preferably $NR_1R_2$ is $NHR_1$ where $R_1$ is as above.

The following compounds and their salts(preferably pharmaceutically acceptable) are particularly preferred:

1-(2,6-difluorobenzyl)-4-(methylamino)-1H-1,2,3-triazolo[4,5-c]pyridine,
4-amino-1-(2,6-difluorobenzyl)-1H-1,2,3-triazolo[4,5-c]pyridine, 1-(2,6-difluorobenzyl)-4-(ethylamino)-1H-1,2,3-triazolo[4,5-c]pyridine,
1-(2,6-difluorobenzyl)-4-(propylamino)-1H-1,2,3-triazolo[4,5-c]pyridine, and
1-(2,6-difluorobenzyl)-4-(dimethylamino)-1H-1,2,3-triazolo[triazolo[4,5-c]pyridine.

Two compounds, namely, 1-(2,6-difluorobenzyl)-4-(methylamino)1H-1,2,3-triazolo[4,5-c]pyridine and 4-amino-1-(2,6-difluorobenzyl)-1H-1,2,3-triazolo[4,5-c]pyridine are particularly preferred because both are potent anticonvulsants and are free of side effects at high multiples of the active dose.

Suitable acid addition salts of the compounds of formula I include those formed with both organic and inorganic acids. Such acid addition salts will normally be pharmaceutically acceptable.

Thus, preferred salts include those formed from hydrohalic, e.g., hydrochloric, sulfuric, citric, isethionic, tartaric, phosphoric, lactic, pyruvic, acetic, succinic, oxalic, fumaric, maleic, lactobionic, oxaloacetic, methanesulfonic, p-toluenesulfonic and benzenesulfonic acids.

There is also provided the first medical use of the novel compounds of the present invention or pharmaceutically acceptable salts thereof, as hereinbefore defined. Preferably this will be for the treatment of epilepsy, in mammals such as humans. The compounds of the present invention have phenytoin like activity and are particularly useful in the treatment of primary generalized tonic-clonic (grand mal) epilepsy.

In a further aspect, there are provided pharmaceutical formulations comprising a compound of the present invention in admixture with a pharmaceutically acceptable carrier.

The pharmaceutically acceptable carriers present in the compositions of this invention are materials recommended for the purpose of administering the medicament. These may be liquid or solid materials, which are otherwise inert or medically acceptable and are compatible with the active ingredients.

These pharmaceutical compositions may advantageously be given orally, but may also be given parenterally, used as a suppository, or applied topically as an ointment, cream or powder. Oral and parenteral administration of the compositions are preferred.

For oral administration, fine powders or granules will contain diluting, dispersing and/or surface active agents, and may be presented in a draught, in water or in a syrup, in capsules or sachets in the dry state or in non-aqueous suspension wherein suspending agents may be included, or in a suspension in water or syrup. Where desirable or necessary, flavouring, preserving, suspending, thickening or emulsifying agents can be included.

For parenteral administration, the compounds may be presented in sterile aqueous injection solutions which may contain anti-oxidants or buffers.

As stated above, the free base or a salt thereof may be administered in its pure form unassociated with other derivatives, in which case a capsule or sachet is the preferred carrier.

Alternatively the active compound may be presented in a pure form as an effective unit dosage, for instance compressed as a tablet or the like.

Other compounds which may be included are, for example, medically inert ingredients, e.g., solid and liquid diluents such as lactose, starch or calcium phosphate for tablet or capsule; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Tablets or other forms of presentation provided in discrete units may conveniently contain an amount of a novel compound as hereinbefore defined which is effective at such dosage or a multiple of the same, for instance, units containing 5mg to 500 mg, usually around 10 mg to 250 mg.

The pharmaceutical compositions of the present invention will be prepared by the admixture of a novel compound or pharmaceutically acceptable salt thereof as hereinbefore defined with a pharmaceutically acceptable carrier. Conventional pharmaceutical excipients may be admixed as required.

The present invention provides a method of treatment of CNS disorders such as convulsions, particularly epilepsy, in mammals, by the administration of a non-toxic therapeutically effective amount of a compound of formula I or a pharmaceutically acceptable salt, or a composition as hereinbefore defined.

Preferably the mammal is a human.

Before commencement of the treatment the mammal in question will, in general, have been identified as suffering from a CNS disorder, particularly epilepsy.

Thus in a preferred embodiment of the present invention, there is provided a method of treatment of epilepsy in humans, comprising the administration to a human in need thereof or a non-toxic therapeutically effective amount of a compound of the formula I or a pharmaceutically acceptable salt, or a composition as hereinbefore defined.

As indicated above, the compounds of the formula I are generally useful in treating such disorders by administration to the human or animal recipient by a route selected from oral, parenteral (including subcutaneous, intradermal, intramuscular and intravenous) and rectal. The size of an effective dose of a compound will depend upon a number of factors including the mammal under treatment (for example cat, dog or human), the type of epilepsy involved for example grand mal, focal seizures and psychomotor convulsions, the severity of the condition to be treated and the route of administration, and will ultimately be at the discretion of the attendant physician. In guiding him in assessing the efficacy and acceptability of a regimen the physician will have recourse to changes in the recipient's gross condition as treatment progresses.

Such an effective epileptic treatment dose will generally be in the range 0.3 to 15 mg/kg bodyweight of animal or human recipient given three times per day, preferably in the range 0.5 to 7 mg/kg bodyweight and most preferably in the range of 1 to 2 mg/kg bodyweight. For the average human of 70 kg bodyweight at 1.0 mg/kg the dose would be 70 mg. Unless otherwise indicated all weights are calculated as the hydrochloride of formula I. For other salts the figures would be amended proportionately. The desired dose may be preferably presented as between two and four sub-doses administered at appropriate intervals throughout the day.

The present invention also provides a process for the preparation of a compound of formula I, which process comprises the reaction of an amine $HNR_1R_2$ with a compound of formula II

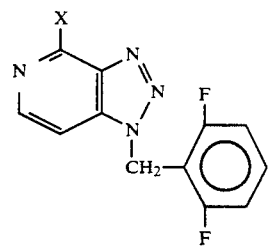

where $R_1$ and $R_2$ are as hereinbefore defined and X is a leaving group.

Compounds of formula II can be prepared by reacting the appropriate diaminopyridines of formula III

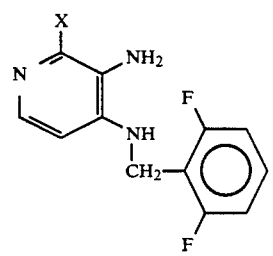

where X is as hereinbefore defined with sodium nitrite in hydrohalic acid, particularly hydrochloric acid.

Compounds of formula III can be prepared by reductive halogenation of a compound of formula IV

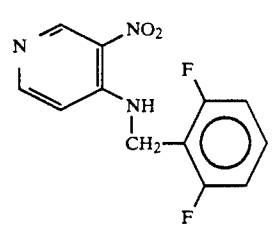

by treating, for example, with stnanous chloride in hot concentrated hydrochloric acid.

Compounds of formula IV can be obtained by reacting compounds of formula V, wherein $R_4$ is halogen, preferably chloro, or OR where R is $C_{1-6}$ alkyl, preferably ethyl,

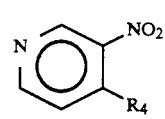

with the appropriate benzyl amine, preferably 2,6-difluorobenzylamine.

Compounds of formula V can be prepared from 4-hydroxypyridine by nitrating with fuming nitric acid and reacting the resulting 4-hydroxy-3-nitropyridine with phosphorous pentachloride, followed by reaction with an appropriate alcohol.

The reaction of a compound of formula II with a mono or disubstituted amine will take place in any suitable solvent, preferably this will be a polar solvent such as a $C_{1-4}$ alkanol, water or acetonitrile. Where appropriate the amine may be used as co-solvent. The reaction will be carried out at non-extreme temperatures e.g., 0°–180° C. suitably at 15°–120° C. and conveniently at room temperature.

Suitable leaving groups X include halogen, $C_{1-6}$ alkylthio, $C_{6-10}$ arylthio, $C_{7-12}$ aralkylthio or $C_{1-4}$ alkyl-, phenyl-, benzyl-, phenylethyl- or naphthylmethyl- substituted sulphonyl or sulphinyl. Preferred leaving groups include halogen, particularly chlorine.

Alternatively compounds of formula II can be prepared by the reaction of a compound formula VI with a compound of formula VII (Aldrich)

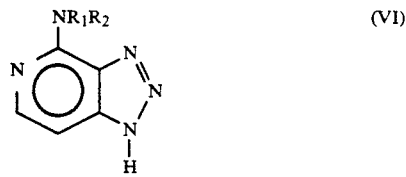
(VI)

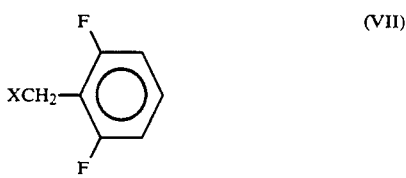
(VII)

wherein $R_1$ $R_2$ and X are hereinbefore defined.

The triazolo[4,5-c] pyridines of formula (VI) can be prepared in a manner analogous to the preparation of formula (II) by reacting a compound of formula VIII

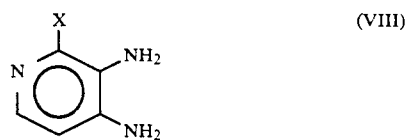
(VIII)

with sodium nitrite in hydrohalic acid and corresponding amination, with suitable aminating agents.

The following examples serve to illustrate the present invention, and should not be construed as limiting thereof.

EXAMPLE 1

Preparation of
1-(2,6-difluorobenzyl)-4-(methylamino)-1H-1,2,3-triazolo4,5-c1 pyridine

A Preparation of
4-[(2,6-difluorobenzyl)amino1-3-nitropyridine

A mixture of 4-chloro-3-nitropyridine[1] (6.67g, 42.1 mmol), 2,6-difluorobenzylamine[2] (7.64g, 42.5 mmol) and water/dioxane (8:3) (110ml) was stirred at ambient temperature for 30 min. The reaction mixture was cooled in an ice-bath and triethylamine (50ml) was added and the mixture was stirred at ambient temperature for 3 days. The reaction was spin evaporated in vacuo. The residue was dissolved in dichloromethane(400 mL) and washed with water(4×250 mL), and the combined extracts were evaporated in vacuo. The solid was dissolved in dichloromethane(500 mL) and added to Silica Gel 60. This mixture was spin evaporated in vacuo, and the residual solid was added to a column of Silica Gel 60 wetted with ethyl acetate: hexane (1:1). The column was eluted with ethyl acetate:- hexane(1:1) using flash chromatography. The appropriate fractions were combined and spin evaporated in vacuo to give 6.50 g(58%) of 4-[(2,6-difluorobenzyl) amino]-3-nitropyridine, mp.=148°–152° C.; $1_H$ NMR(DMSO-$d_6$ ): δ9.01(s, 1H, pyridine H-2), 8.64(t, 1H, J=6.1 Hz, NH), 8.31(d, 1H, J=6.2 Hz, pyridine H-6), 7.50–7.05(m, 3H, Ar), 7.00(d, 1H, J=6.2 Hz, pyridine H-5), 4.72(d, 2H, J=6.1 Hz, $CH_2Ar$).

1. D. M. Houston, E. K. Dolence, B. T. Keller, U. P. Thombre and R. T. Borchardt, *J. Med. Chem.* 28, 467(1985).
2. J. L. Kelley, M. P. Krochmal, J. A. Linn, E. W. Mclean, and F. E. Soroko, *J. Med. Chem.* 31, 1005(1988).

B Preparation of
3-Amino-2-chloro-4(2.6-difluorobenzvl)amino]pyridine

Procedure: A 3-neck 5-L flask, equipped with a thermometer, reflux condenser, nitrogen inlet and a mechanical stirrer was charged with 4-[(2,6-difluorobenzyl)amino]3-nitropyridine(146g, 0.55mol) and concentrated hydrochloric acid(1.4L, 16.8mol). The solution was heated on a steam bath to 90° C. and stannous chloride dihydrate(659g, 2.92mol) was added portionwise. After heating the suspension at 90° C. for 1.5 hours, the condenser was replaced with a distillation apparatus and approximately 1.5L of $H_2O$ removed by distillation at 100mm Hg. The remaining suspension was cooled in an ice bath and neutralized to pH 7 with concentrated ammonium hydroxide. The pasty solid was collected by filtration and dried overnight on a Buechner funnel. The still damp solid was transferred to a 12-L flask equipped with a mechanical stirrer and reflux condenser and charged with ethyl acetate. With rapid stirring, the suspension was heated at reflux for 3.5 hours on a steam bath, cooled slightly, filtered using positive nitrogen pressure, and the filtrate concentrated in vacuo. The resulting oily solid was slurried in ethyl ether, solids collected by filtration and dried overnight on a Buechner funnel to yield 123g (83.1%) of 3-amino-2-chloro-4-[(2,6-difluorobenzyl)amino]pyridine. TLC (silica gel, EtOAc/ether, 1:1) $R_f$=0.71; mp=221°–2230° C.; 1H NMR (DMSO-$d_6$): 4.36(d,J=5.1 Hz, 2H, $CH_2$), 4.84 (s, 2H, $NH_2$), 6.06(t, J=5.1 Hz, 1H, NH), 6.54(d,J=5.4Hz, 1H, C-5H), 7.01–7.65 (m, 3H, C-3'H, C-4'H, C-5'H), 7.44 (d, J=5.3 Hx, 1H, C-6H).

Elemental analysis calculated C, 53.45; H, 3.74; N, 15.58; Cl, 13.15; F, 14.08; .Found: C,53.6; H, 3.69; N, 15.51; Cl, 13.09; F, 14.12.

C Preparation of
1-(2.6-difluorobenzyl)-4-(methylamino)-1H-1,2,3triazolo[4,5-c]pyridine hydrochloride Procedure: A 5-L flask equipped with mechanical stirrer, condenser and thermometer was charged with concentrated hydrochloric acid (160mL), 1N hydrochloric acid (430 mL) and absolute ethanol (1230 mL). The solution was cooled in an ice bath to 5° C. and 3-amino-2-chloro[(2,6-difluorobenzyl)amino]-pyridine(45 g, 0.17 mol) was added portionwise, followed by the addition of sodium nitrite(14 g, 0.20 mol). After stirring for 35 minutes at 5° C., 40% aqueous methylamine(1.08L, 13.8 mol) was added and the solution heated at reflux for 30 minutes. The reaction was cooled in the freezer overnight, the precipitated solid collected by filtration, washed with ice water and dried overnight on a Buechner funnel to afford the title compound as the free base in quantitative yield.

A 2-L flask fitted with a mechanical stirrer, condenser and thermometer was charged with absolute ethanol (1.0L) and heated to reflux. After removal of the heating mantle, the free base was immediately added followed by concentrated hydrochloric acid (30 mL).

The resulting suspension was cooled in an ice bath for 3 hours, solids collected by filtration, washed with chilled ethanol (300 mL) and dried overnight in a vacuum oven at 50° C. to produce 35 g (67%) of 1-(2,6-difluorobenzyl)-4-(methylamino)-1H-1,2,3-triazolo[4,5-c]pyridine hydrochloride. TLC (silica gel, EtOAc:Et₂O, 1:1) Rf=0.49; mp =297°-298° C.; $1_H$ NMR (DMSO-d₆): 3.07 (s, 3H, CH₃), 5.95 (s, 2H, CH₂) 7.04(d, J=6.6 Hz, 1H, C-7H), 7.19 (t, 2H, C-3'H, C-5'H), 7.51 (m, 1H, C-4'H), 7.89 (d, J=6.6 Hz, 2H, C-6H), 8.88 (br s, 1H, NH).

Elemental analysis calculated: C, 50.09; H, 3.88; N, 22.47; Cl, 11.37; F, 12.19. Found: C, 50.11; H, 3.90; N, 22.42; Cl, 11.45; F, 12.08.

EXAMPLE 2

Preparation of 1-(2,6-difluorobenzyl)-4-(ethylamino)-1H-1,2,3-triazolo[4,5-c]pyridine hydrochloride This compound was prepared in an analogous manner to that of Example 1C with the replacement of methylamine with ethylamine. It was precipitated from a solution of the free base in EtOH with concentrated HCl. Yield 87%, mp. =285°-289° C.; $1_H$NMR(DMSO-d₆): δ1.25(t, J=7 Hz, 3H, CH₃), 3.62(br s, 2H, CH₂CH₃, 6.02(s, 2H, CH₂Ar), 7.10-7.26(m, 2H, C-3'H, and C-5'H), 7.29(d, J=7 Hz, 1H, C-7H), 7.46-7.61(m, 1H, C-4'H), 7.86(d, J=7 Hz, 1H, C-6H), 10.2(br s, 1H, NH), 13.5(br s, 1H, H+).

Elemental analysis calculated: C, 51.62; H, 4.33; N, 21.50; Cl, 10.88. Found: C, 51.69; H, 4.34; N, 21.50; Cl, 10.97.

EXAMPLE 3

Preparation of 1-(2,6-difluorobenzyl)-4-(propylamino)-1H-1,2,3-triazolo[4,5-c]pyridine hydrochloride This compound was prepared in an analogous manner to that of Example 1C with the replacement of methylamine with propylamine. It was precipitated from a solution of the free base in EtOH with concentrated HCl. Yield 56%, mp.=268°-273° C.; $1_H$ NMR(DMSO-d₆): δ0.93(t, J=7 Hz, 3H, CH₃), 1.66(sextet, J=7 Hz, 2H, CH₂CH₃), 3.52(br s, 2H, NCH₂CH₃, 6.02(s, 2H, CH₂Ar), 7.16-7.24(m, 2H, C-3'H, and C-5'H), 7.29(d, J=7 Hz, 1H, C-7H), 7.46-7.61(m, 1H, C-4'H), 7.86(d, J=7 Hz, 1H, C-6H), 10.24(br s, 1H, NH), 13.5(br s, 1H, H+).

Elemental analysis calculated: C, 53.02; H, 4.75; N, 20.61; Cl, 10.44. Found: C, 52.82; H, 4.71; N, 20.50; Cl, 10.50.

EXAMPLE 4

Preparation of 1-(2,6-difluorobenzyl)-4-(dimethylamino)-1H-1,2,3-triazolo[4,5-c]pyridine hydrochloride This compound was prepared in an analogous manner to that of Example 1C with the replacement of methylamine with anhydrous dimethylamine. It was precipitated from a solution of the free base in EtOH with concentrated HCl. The compound was recrystallized from hot H₂O with dilute HCl. Yield 81%, mp. =240°-249° C.; ¹H NMR(DMSO-d₆): 3.64(br s, 6H, CH3, 6.04(s, 2H, CH₂Ar), 7.15-7.25(m, 2H, C-3'H, and C-5'H), 7.32(d, J=7 Hz, 1H, C-7H), 7.45-7.60(m, 1H, C-4'H), 7.91(d, J=7 Hz, 1H, C-6H).

Elemental analysis calculated: C, 51.62; H, 4.33; N, 21.50; Cl, 10.88. Found: C, 51.70; H, 4.28; N, 21.56; Cl, 10.92.

EXAMPLE 5

Preparation of 4-amino-1-(2,6,-difluorobenzyl)-1H-1,2,3-triazolo[4.5-c]pyridine hydrochloride Procedure: A 3-L flask equipped with a thermometer and mechanical stirrer was charged with concentrated hydrochloric acid (140 mL), 1N hydrochloric acid (380 mL) and absolute ethanol (1.10L) and cooled to 5° C. in an ice bath. 3-Amino-2-chloro-4-[(2,6-difluorobenzyl)amino]pyridine(40 g, 0.15mol)(from example 1B) was added followed by the addition of sodium nitrite(13.3 g, 0.19 mol). The solution was stirred for 35 minutes at 5° C., ammonium hydroxide was added to pH9, and the solution extracted with chloroform (2×1.00L). The combined organic extracts were dried (sodium sulphate) and concentrated to produce 4-chloro-1-(2,6-difluorobenzyl)-1H-1,2,3- triazolo[4,5-c]pyridine as a damp pink solid in quantitative yield, sufficiently pure for further reaction. A sample was purified by flash column chromatography to give the analytical sample, mp.=133°-139° C. ¹H NMR (DMSO-d₆): 6.10 (s, 2H, CH₂), 7.10-7.65(m, 3H, C-3'H, C-4'H, C-5'H), 7.95 (d, J=5.9 Hz, 1H, C-7H), 8.43 (d, J=5.9 Hz, 1H, C-6H).

Elemental Analysis calculated: C, 51.35; H, 2.51; N, 19.96; Cl, 12.63. Found: C, 51.33; H, 2.55; N, 19.93; Cl, 12.56.

The isolated solid was dissolved in ammonia saturated ethanol (2.0oL), divided into two approximately equal volumes and poured into two 2-L glass-lined bombs. The bombs were heated to 120° C. for 40h, cooled, and the solids collected by filtration to produce 4-amino-1-(2,6-difluorobenzyl)-1H-1,2,3-triazolo[4,5-c]pyridine as the free base in 95% yield. A 2-L flask fitted with a condenser was charged with the free base and 2-methoxyethanol (1.0L), and the suspension was heated to 105° C. to obtain solution. Concentrated hydrochloric acid (400 mL) was added carefully through the condenser, the solution was cooled and the white solid was collected by filtration to produce 35g (80%) of 4-amino-1-(2,6-difluorobenzyl)-1H-1,2,3-triazolo[4,5-c]pyridine hydrochloride. TLC (silica gel, EtOAc:Et₂O, 1:1) R_f=0.10, mp.=283°-285° C.; 1H NMR (DMSO-d₆): 6.04 (s, 2H, CH₂), 7.17 (m, 2H, C-3'H, C-5'H), 7.35 (d, J=7.1 Hz, 1H, C-7H), 7.53 (m, 1H, C-4'H), 7.96 (d, J=7.1 Hz, 1H-C-6H), 9.2-10.0 (br s, 2H, NH₂).

Elemental Analysis calculated: C, 48.41; H, 3.39; N, 23.53; Cl, 11.91; F, 12.76. Found: C, 48.43; H, 3.41; N, 23.47; Cl, 11.93; F, 12.78.

Pharmacological Activity

The anticonvulsant activity of certain compounds of examples 1 and 2 of the present invention were determined by a standard maximal electroshock test (MES); that described by L.A. Woodbury and V. D. Davenport, *Arch.Int.Pharmacodyn*, 92 97 (1952).

| COMPOUND OF EXAMPLE NO | SALT | ED50.P.O. (mg/kg) |
| --- | --- | --- |
| 1 | HCl | 5.3 |
| 2 | HCl | 7.8 |
| 3 | HCl | 17.5 |
| 4 | HCl | 7.8 |

| COMPOUND OF EXAMPLE NO | SALT | ED50.P.O. (mg/kg) |
|---|---|---|
| 5 | HCl | 3.7 |

FORMULATION EXAMPLES

In the formulation examples that follow, Compound A is; 4-amino-1-(2,6-difluorobenzyl)-1H-1,2,3-Triazolo[4,5-c]pyridine hydrochloride, and Compound B is; 1-(2,6-difluorobenzyl)-4-(methylamino)-1H-1,2,3-triazolo[4,5-c]pyridine hydrochloride.

| I - Formulation | |
|---|---|
| Compound A | 25 mg |
| Corn starch | 45 mg |
| Polyvinylpyrrolidone | 6 mg |
| Stearic acid | 12 mg |
| Magnesium stearate | 2 mg |
| Lactose qs to | 300 mg |

The compound is finely ground and intimately mixed with the powdered excipients lactose and corn starch. The powders are wetted with a solution of polyvinylpyrrolidone dissolved in purified water and denatured alcohol to form granules. The granules are dried and mixed with the powdered stearic acid and magnesium stearate. The formulation is then compressed into tablets weighing approximately 300 mg each.

| II - Capsule | |
|---|---|
| Compound A | 25 mg |
| Corn starch | 45 mg |
| Stearic acid | 12 mg |
| Lactose qs to | 300 mg |

The finely ground active ingredient is mixed with the powdered exipients lactose and corn starch, and stearic acid and filled into hard-shell gelatin capsules.

| III - Suppository | |
|---|---|
| Compound A | 25 mg |
| Cocoa butter | 1975 mg |

The cocoa butter is heated to melting and the active ingredient is dispersed by thorough mixing. The mass is then formed into suppositories weighing approximately 2,000 mg each.

| IV - Injection | |
|---|---|
| Compound A | 25 mg |
| Sodium chloride | 0.9% |
| Preservative | 0.1% |
| Hydrochloric acid or sodium hydroxide | as need for pH adjustment |
| Water for injection | qs to 2-3 ml |

The active ingredient sodium chloride, and preservative are dissolved in a portion of the water for injection. The pH of the solution is adjusted with hydrochloric acid or sodium hydroxide. Water for injection is added to final volume and the solution is thoroughly mixed. The solution is sterilized by filtration through a 0.22 micrometer membrane filter and aseptically filled into sterile containers.

| V - Syrup | |
|---|---|
| Compound B | 15 mg |
| Glycerin | 500 mg |
| Sucrose | 3500 mg |
| Flavouring agent | qs |
| Colouring agent | qs |
| Preserving agent | 0.1% |
| Purified water | qs to 5 ml |

The active ingredient and sucrose are dissolved in the glycerin and a portion of the purified water. The preserving agent is dissolved in another portion of hot purified water, and then the colouring agent is added and dissolved. The two solutions are mixed and cooled before the flavouring agent is added. Purified water is added to final volume. The resulting syrup is thoroughly mixed.

The compound of Example 5, 4-amino-1-(2,6-difluorobenzyl)-1H-1,2,3-triazolo[4,5-c]pyridine hydrochloride has also been found to be active in a neutrophil adhesion assay in vitro and in the acute anti-inflammatory in vivo assay by the carrageenan pleurisy test in rats both orally and intraperitoneally. Therefore, 4-amino-1-(2,6-difluorobenzyl)-1H-1,2,3-triazolo[4,5-c]-pyridine and its pharmaceutically acceptable salts, especially the hydrochloride salt, are useful in treating inflammatory conditions in mammals, especially humans.

What I claim is:

1. A compound of formula I

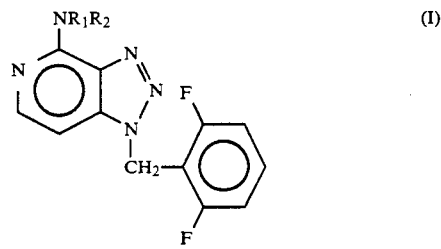

(I)

wherein $R_1$ and $R_2$ may be the same or different and are selected from hydrogen and $C_{1-4}$ straight or branched alkyl, or a salt thereof.

2. The compound of claim 1 wherein $R_1$ is hydrogen.

3. The compound of claim 1 or 2 wherein the salt is a pharmaceutically acceptable salt.

4. The compound of claim 1 or 2 wherein the salt is a pharmaceutically acceptable acid addition salt.

5. The compound of claim 3 or 4 wherein the salt is the hydrochloride salt.

6. 4-Amino-1-(2,6-difluorobenzyl)-1H-1,2,3-triazolo[4,5-c]pyridine or a pharmaceutically acceptable acid addition salt thereof.

7. 4-Amino-1-(2,6-difluorobenzyl)-1H-1,2,3-triazolo[4,5-c]pyridine hydrochloride.

8. 1-(2,6-Difluorobenzyl)-4-(methylamino)-1H-1,2,3-triazolo[4,5-c]-pyridine or a pharmaceutically acceptable acid addition salt thereof.

9. 1-(2,6-Difluorobenzyl)-4-(methylamino)-1H-1,2,3-triazolo[4,5-c]-pyridine hydrochloride.

10. 1-(2,6-Difluorobenzyl)-4-(ethylamino)-1H-1,2,3-triazolo[4,5-c]-pyridine hydrochloride.

11. 1-(2,6-Difluorobenzyl)-4-(propylamino)-1H-1,2,3-triazolo[4,5-c]-pyridine hydrochloride.

12. 1-(2,6-Difluorobenzyl)-4-(dimethylamino)-1H-1,2,3-triazolo[4,5-c]-pyridine hydrochloride.

13. A pharmaceutical formulation comprising a compound of formula I wherein $R_1$ and $R_2$ may be the same or different and are selected from hydrogen and $C_{1-4}$ straight or branched alkyl, or a pharmaceutically acceptable salt thereof and a pharmaceutically acceptable carrier therefor.

14. A pharmaceutical formulation of claim 13 wherein $R_1$ is hydrogen.

15. A pharmaceutical formulation of claim 13 wherein the compound is 4-amino-1-(2,6-difluorobenzyl)-1H-1,2,3-triazolo[ 4,5-c]pyridine or a pharmaceutically acceptable acid addition salt thereof.

16. A pharmaceutical formulation of claim 13 wherein the compound is 1-(2,6-difluorobenzyl)-4-(methylamino)-1H-1,2,3-triazolo[4,5-c]-pyridine or a pharmaceutically acceptable acid addition salt thereof.

17. The pharmaceutical formulation of claim 15 wherein the pharmaceutically acceptable salt is the hydrochloride salt.

18. The pharmaceutical formulation of claim 16 wherein the pharmaceutically acceptable salt is the hydrochloride salt.

19. A pharmaceutical formulation of claim 15 which is a tablet or capsule.

20. A pharmaceutical formulation of claim 16 which is a tablet or capsule.

21. The method of treating a mammal which has been identified as having had convulsions, comprising the step of administering to said mammal an effective treatment amount of the compound of claim 1.

22. The method of claim 21 which comprises the oral administration of a tablet or capsule containing 4-amino-1-(2,6-difluorobenzyl)-1H-1,2,3-triazolo[4,5-c]pyridine or a pharmaceutically acceptable salt thereof.

23. The method of claim 21 which comprises the oral administration of a tablet or capsule containing 1-(2,6-difluorobenzyl)-4-(methylamino)-1H1,2,3-triazolo[4,5-c] -pyridine or a pharmaceutically acceptable salt thereof.

24. The method of claim 21 which comprises the parenteral administration of 4-amino-1-(2,6-difluorobenzyl)-1H-1,2,3-triazolo[4,5-c]pyridine or a pharmaceutically acceptable salt thereof.

25. The method of claim 21 which comprises the parenteral administration of 1-(2,6-difluorobenzyl)-4-(methylamino)-1H-1,2,3-triazolo[4,5-c]-pyridine or a pharmaceutically acceptable salt thereof.

26. The method of claim 21 wherein said mammal is a human.

27. A method of treating epilepsy in a human which comprises administering to said human a therapeutically effective amount of a compound of formula I wherein $R_1$ and $R_2$ may be the same or different and are selected from hydrogen and $C_{1-4}$ straight or branched alkyl, or a pharmaceutically acceptable salt thereof and a pharmaceutically acceptable carrier therefor.

28. A method of treating epilepsy in a human which comprises administering to said human a therapeutically effective amount of a pharmaceutically acceptable salt of 4-amino-1-(2,6-difluorobenzyl)-1H-1,2,3-triazolo[4,5-c]pyridine.

29. A method of treating epilepsy in a human which comprises administering to said human a therapeutically effective amount of a pharmaceutically acceptable salt of 1-(2,6-difluorobenzyl)-4-(methylamino)-1H-1,2,3-triazolo[4,5-c]-pyridine.

30. A unit dose of the compound or salt of claim 6 or 7, containing 5 to 500 mg of the compound or salt.

31. A unit dose of the compound or salt of claim 30, containing 10 to 250 mg of the compound or salt.

32. The unit dose of claim 30, in which the unit dose is in the form of a capsule or tablet.

33. The unit dose of claim 31, in which the unit dose is in the form of a capsule or tablet.

* * * * *